United States Patent [19]

Baldo et al.

[11] Patent Number: 5,099,857

[45] Date of Patent: Mar. 31, 1992

[54] MEDICAL TESTING DEVICE WITH CALIBRATED INDICIA

[75] Inventors: Brian A. Baldo, Pymble; Euan R. Tovey, Petersham, both of Australia

[73] Assignee: Northern Sydney Area Health Service, St. Leonards, Australia

[21] Appl. No.: 449,825

[22] PCT Filed: May 27, 1988

[86] PCT No.: PCT/AU88/00163

§ 371 Date: Nov. 29, 1989

§ 102(e) Date: Nov. 29, 1989

[87] PCT Pub. No.: WO88/09149

PCT Pub. Date: Dec. 1, 1988

[30] Foreign Application Priority Data

May 29, 1987 [AU] Australia ............................ PI2229

[51] Int. Cl.⁵ ................................................ A61B 5/00
[52] U.S. Cl. ......................................... 128/743; 604/46
[58] Field of Search ............................ 604/46, 47, 51; 128/743; 206/364, 367, 439

[56] References Cited

U.S. PATENT DOCUMENTS

| | | | |
|---|---|---|---|
| 2,190,745 | 2/1940 | Vollmer | 128/743 |
| 2,304,817 | 12/1942 | Grozin | 128/743 |
| 2,817,336 | 12/1957 | Kravitz et al. | |
| 2,841,138 | 7/1958 | Laub | 128/743 |
| 2,893,392 | 7/1959 | Wagner et al. | 128/743 |
| 2,974,787 | 3/1961 | Cooper | |
| 3,194,237 | 7/1965 | Rubin | |
| 3,512,520 | 5/1970 | Cowan | |
| 3,894,531 | 7/1975 | Saunders, Jr. | 128/743 |
| 4,205,689 | 6/1980 | Brennan | |
| 4,222,392 | 9/1980 | Brennan | |
| 4,292,979 | 10/1981 | Inglefield, Jr. et al. | |
| 4,390,027 | 6/1983 | Alani et al. | |
| 4,453,926 | 6/1984 | Galy | |

FOREIGN PATENT DOCUMENTS

| | | |
|---|---|---|
| 66735 | 1/1984 | Australia . |
| 0081975 | 6/1983 | European Pat. Off. . |
| 2444379 | 3/1976 | Fed. Rep. of Germany . |
| 1301930 | 1/1973 | United Kingdom . |
| WO81/00199 | 2/1981 | World Int. Prop. O. . |

Primary Examiner—John D. Yasko
Assistant Examiner—Anthony Gutowski
Attorney, Agent, or Firm—Lowe, Price, LeBlanc & Becker

[57] ABSTRACT

A disposable medical testing device (17) adapted to be held against the skin of a patient, which enables the performance of skin testing for the diagnosis of both immediate hypersensitivity and delayed hypersensitivity immune reactions. The device is comprised of a hollow body with a sealed chamber in which is mounted a movable needle (3) capable of penetrating a patient's skin to a predetermined depth and a test reagent container (2). The device (17) is manipulable by a user to reduce the volume of the chamber and moving the needle thus releasing the reagent and causing penetration of the skin. The released reagent is delivered to the skin penetration site, and any resulting skin reaction is observed and recorded. Embodiments of the invention marked with a calibrated scale on a releasable transparent layer and details of patient and test date which allow multiple antigen tests to be performed are also disclosed. A method of testing for immune response using the device (17) is also disclosed.

21 Claims, 4 Drawing Sheets

Figure 8
Figure 9
Figure 10
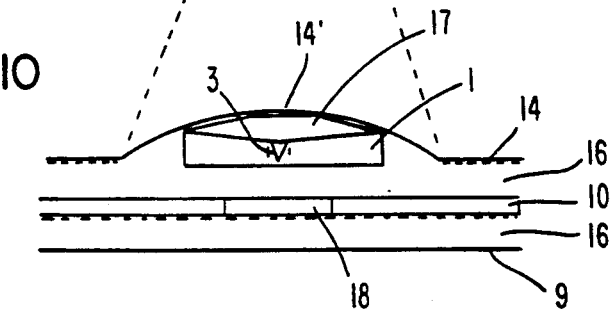
Figure 11

MEDICAL TESTING DEVICE WITH CALIBRATED INDICIA

TECHNICAL FIELD

The present invention relates to a novel disposable testing device for skin testing human subjects for immediate hypersensitivity (allergic) or delayed hypersensitivity (cell-mediated) immune reactions. The testing device comprises one or more separate needles each in combination with a small reservoir of antigen test reagent in a strip, sheet or patch format.

BACKGROUND ART

Skin testing for allergy has conventionally been performed by putting a small drop of the suspected allergen on the back or the forearm of the subject and then exposing the underlying tissue by pricking the skin with a needle. An inflammatory response occurring within about 10-15 minutes indicates allergy to the suspected substance. Commonly, allergy to between 5 and 20 suspected substances may be tested in this way at any one time. This test commonly called the "skin-prick test", has remained essentially unchanged in its design since it was first introduced over 70 years ago. The method, still widely used by specialists in the field of allergic disease, is not as popular with general practitioners since it takes up valuable consultation time in the surgery, is uncomfortable for the subject and is costly to provide, especially if it is only done occasionally. Prick testing also requires some technical skill and is quite labour intensive. However, it is the most reliable method of those used to diagnose allergy and gives a result within 10 to 30 minutes of starting the test.

In a similar manner, testing for cell-mediated immunity may be performed by either injecting a small quantity of antigen under the surface of the skin using a needle and syringe or by puncturing the skin and allowing antigen solution to passively infiltrate the puncture site. The skin reaction, which is an index of the patient's ability to mount an immune response to the test antigen, is usually measured many hours to several days later.

In the last 15 years, an alternative method of testing for allergy using an in vitro assay has been introduced. The assay requires the use of serum, the reagents used are costly, assays are only performed by specialist pathology laboratories, and several days may elapse before a result is known. Because of the cost, the number of tests which can be performed is often limited to 4 suspected allergens. Only in rare circumstances do such in vitro assays offer any advantages over skin tests, for example where the skin of a patient with eczema is highly inflamed, or when the patient is taking a particular drug which interferes with the skin test response. The correlation between results from skin prick tests and in vitro tests is only about 70% and there are several reasons why such in vitro tests sometimes produce false negative and false positive reactions. Despite this, these assays are very popular (well over 100 million have been performed internationally), and despite several more companies entering the field recently and the introduction of minor changes in design and/or procedure, no major improvements have been made.

It would be desirable to adapt the skin test to make it more available and acceptable to both patient and physician, and to improve the speed and reliability of the diagnosis of immune-mediated responses. Reduction of the costs of both tests would also, of course, be welcome.

An object of the present invention is to refine the existing methods of skin testing for the diagnosis of both immediate and delayed immune reactions. The procedure when the device of the present invention is employed does not require any specialized technical expertise and is sufficiently simple to be used, without specialised training, by general practitioners (GPs). It is also more acceptable to patients than when conducted according to prior art techniques.

DISCLOSURE OF THE INVENTION

In accordance with the present invention there is provided a medical testing device adapted to be held against the skin of a patient to perform a test, said device comprising a hollow body providing a sealed chamber, a needle mounted within said chamber and movable to extend beyond said body to penetrate a patient's skin to a predetermined depth, a test reagent within said chamber, and wherein said device is manipulable by a user to reduce the volume of said chamber to release said reagent and to cause penetration of said needle by moving the needle to extend beyond said body.

In another aspect, the invention provides a method of testing for an immune response, which method comprises applying to the skin of a patient a medical testing device adapted to be held against the skin, said device comprising a hollow body providing a sealed chamber, a needle mounted within said chamber and movable to extend beyond said body to penetrate a patient's skin to a predetermined depth, a test reagent within said chamber, and wherein said device is manipulable by a user to reduce the volume of said chamber to release said reagent and to cause penetration of said needle by moving the needle to extend beyond said body, manipulating said device to release said reagent on to the skin and to cause penetration of the skin by said needle, observing and recording any skin reaction resulting therefrom after an appropriate time interval.

Generally, the needle will be adapted to penetrate the skin about 1 to 2 mm and may have a plurality of points or be fluted or grooved to enhance flow of the reagent to the skin. To limit the depth to which the needle penetrates the skin, it may be fitted with a collar or be of enlarged cross-section beyond its point or points.

In general, the reagent will be an antigen. However, other components or other reactive compounds may be included in the reagent. Different substances, or dilutions of the same substance with or without control substances such as the vehicle alone, or standard solutions, such as a histamine solution, may be tested concurrently at different skin sites, when the medical testing devices of the invention are incorporated into strips or sheets. Individual patches, strips or sheets may be manufactured as part of a large sheet and separated into single patches, strips or sheets prior to use. In a format where multiple tests are involved, sufficient distance would be allowed between individual antigen/needle units to avoid one test substance interfering with an adjacent test substance. For example, in skin testing for immediate hypersensitivity, a minimum distance between units would be about 20 mm.

The reagent may be conveniently contained within a capsule, reservoir or porous matrix or may contain an additive to form a paste or gel.

It is preferred to include a transparent layer in the device of the invention to both identify the reagent and to record details of the test. Thus, the transparent layer may be printed with identifiers of both the subject tested and of the test substances employed. It is preferably of a material which can be written on and has calibrations to enable the size of the skin reaction to be measured. It is preferably coated on the underside with a low-tack adhesive to secure the device to the skin in use. The adhesive also permits the transparent strip to be affixed to the patient's medical records.

After placement of the strip or patch on the skin, light direct finger pressure on each unit both releases the solution containing the antigen and causes the needle to penetrate the skin to a limited depth insufficient to draw blood. The antigen solution then infiltrates the site of the needle puncture causing a limited exposure of the intradermal or subcutaneous tissues to the antigen. The immunological response to such exposure is determined after the appropriate time, depending on the immune response involved.

BRIEF DESCRIPTION OF THE DRAWINGS

FIGS. 6, 6A, 6B, 6C show various designs of needle points which can be used in the test devices of the invention.

FIG. 8 shows a view from above of the arrangement of a test device of the invention including a number of antigen testing units.

FIG. 9 is a side view of the embodiment of FIG. 8.

FIG. 10 is an exploded enlarged view of one of the antigen testing units of FIGS. 7, 8 and 9.

FIG. 11 shows a view from above of the transparent layer of the test device of FIGS. 8 and 9.

BEST MODES FOR CARRYING OUT THE INVENTION

The following description relates to preferred embodiments of the invention as illustrated in the accompanying drawings and should not be construed as limiting on the claims.

Figure 1:
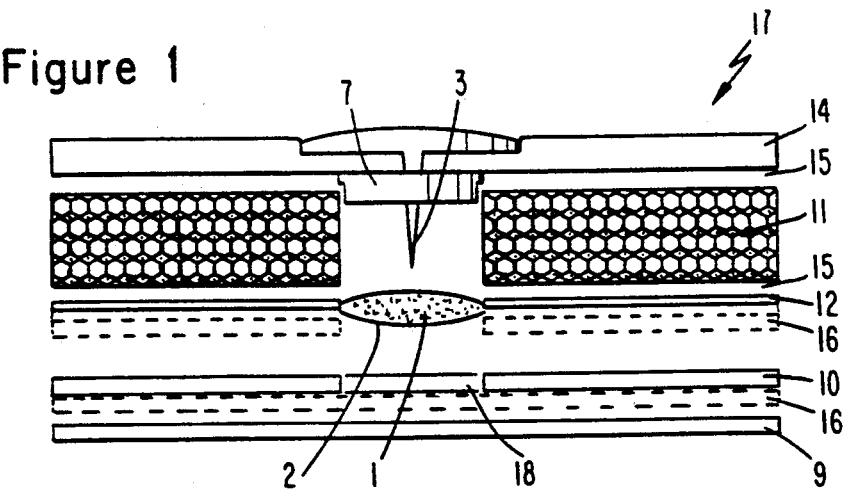
FIG. 1 shows a cross section of the skin test device in accordance with a first embodiment of the invention.

The skin test device (17) of FIG. 1 is made up of an antigen support layer (12) containing one or more (1 illustrated) capsules (2) containing antigen solution (1). Disposed to one side of the layer (12) is a compressible layer (11) and a cover (14). The layer (11) could be made of foam plastic, rubber or be of an air cell construction, and is adhered to support (12) and cover (14) is adhered to layer (11) by means of high-tack adhesive (15). The compressible layer (11) keeps capsule (2) and needle (3) separate when the device (17) is not in use, and keeps the needle above the plane of the patient's skin when uncompressed. It can also provide a physical mattress to house the capsule (2) and the needle (3). The cover (14) incorporates a needle (3) and ensures sterility and adds rigidity. The cover may be made of a material such as plastic, impregnated paper or metal foil. Its upper surface may be colour-coded and/or printed with the name(s) of the antigen(s) and with instructions for use of the device. Alternatively, it may be decorated to render the device more acceptable to children. The needle (3) which ruptures the capsule (2) prior to the needle penetrating the skin is provided with a collar (7) to restrict the depth of penetration of needle (3) into the skin, preferably to about 1 to 2 mm, when the device (17) is in use. A transparent layer (10) and bottom cover (9) are disposed on the side of the support layer (12) opposite the needle (3) with a hole (18) in line with the needle (3). The bottom layer (9), seals, protects and ensures the sterility of the unit. It is removed prior to the start of the test. The removal of this layer exposes a layer of low-tack adhesive (16), shown bonded to the transparent layer (10). The purpose of the adhesive is to temporarily and lightly hold the device to the surface of the skin. The adhesive concerned should not be strong enough to cause discomfort when the device is removed from the skin. Layer (10) is also secured to support layer (12) by means of low-tack adhesive (16). The layer could be made of plastic, cellulose, nylon or other transparent material which can be written on to outline the extent of a skin reaction and to record details of the subject—for example the name, unit number and date. This layer could also be printed with scale markings in mm to enable a skin reaction such as a wheal or flare response to be measured. Low-tack adhesive (16) permits the upper layers to be removed to allow the skin reaction to be viewed through the remaining transparent layer. When the skin reaction has fully developed, it can be measured from the scale or the outline of the reaction can be marked on the transparent layer which may then be removed and kept for record purposes.

Figure 2:
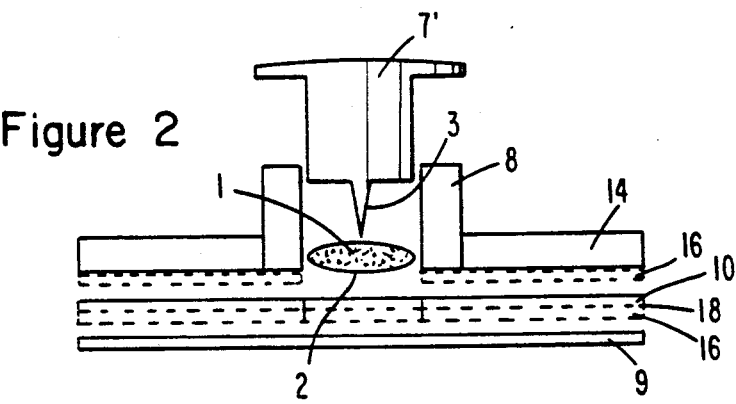
FIG. 2 shows a second embodiment in cross section.

In the embodiment of FIG. 2, needle guides (8) are built into top layer (14). The needle (3) is adapted to fit guide (8) tightly by means of collar (7'). Needle guide (8) also locates capsule (2) of antigen solution (1) between needle (3) and hole (18) in transparent layer (10). The device is sealed by bottom cover (9). Both top cover (14) and bottom cover (9) are affixed to transparent layer (10) by low-tack adhesive (16).

Figure 3:
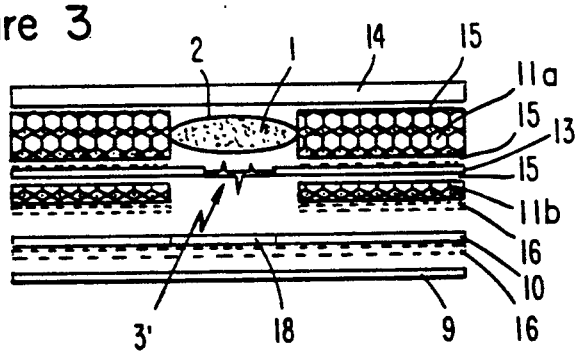
FIG. 3 shows an alternate arrangement of a needle unit applicable to the invention and illustrated in a third embodiment.
Figure 3A:
FIGS. 3A, 3B and 3C respectively depict sectional, bottom and perspective views of the needle depicted in FIG. 3.
Figure 3B:
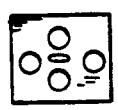
Figure 3C:
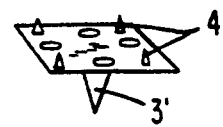

FIGS. 3 and 3A illustrate a further embodiment of the invention where as in the embodiments of FIGS. 1 and 2, a transparent layer (10) is bound to bottom cover (9) and the balance of the device by low-tack adhesive (16). In the embodiment of FIGS. 3 and 3A compressive layers (11) are provided above and below a support layer (13) which holds modified needle (3') and locates needle (3') above hole (18) in transparent layer (10). Compressive layer (11b) away from the transparent layer (10) is thicker than the compressive layer (11a) adjacent transparent layer (10) and carries capsule (2) of antigen solution (1) and locates it above needle (3') and hole (18). Needle (3') carries barbs (4) opposite the needle point which enable capsule (2) to be pierced to release the antigen solution (1). The device has a top cover (14). Layers (14) and (11a) (11b) and (13) are bound together with high-tack adhesive (15).

Figure 4:
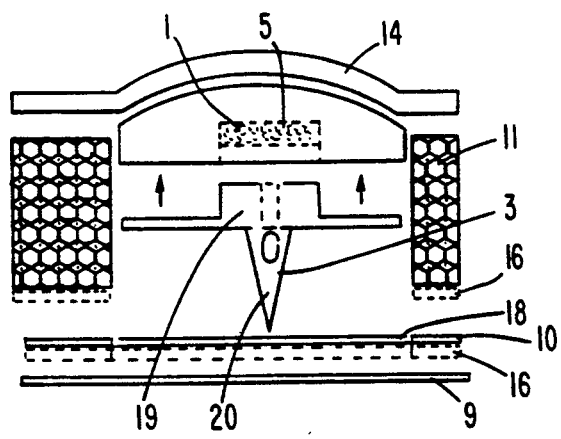
FIG. 4 shows a cross section of fourth embodiment of the invention.

In the embodiment of FIG. 4, the antigen solution (1) is contained in a reservoir (5) so shaped to correspond with a hub (19) in needle (3). Needle (3) has a hollow shaft (20) through which the antigen solution (1) can flow from the reservoir (5) to the skin test site. Needle (3) and reservoir (5) are surrounded by compressible layer (11) and covered by a top covering layer (14). The needle and reservoir are aligned over a hole (18) in transparent layer (10) which is bound to the compressible layer (11) and to bottom cover layer (9) by low-tack adhesive (16).

Figure 5:
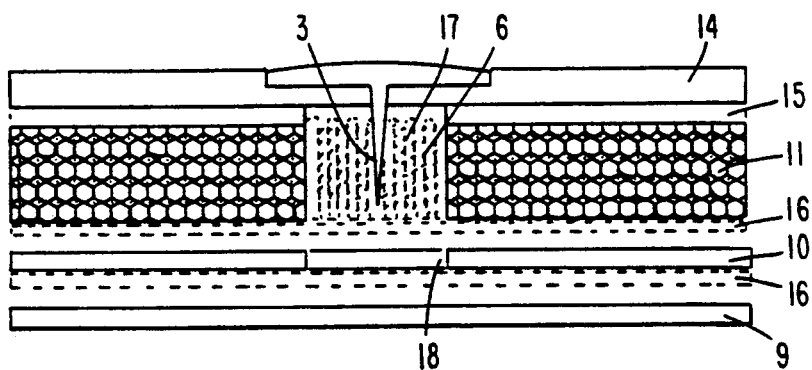
FIG. 5 shows a fifth embodiment in cross section.

FIG. 5 illustrates an embodiment of the invention similar to that described in FIG. 1. In the device of FIG. 5, a compressible porous matrix (6), such as glass fibre or plastic foam, containing the antigen solution replaces the capsule (2) and collar (7) of FIG. 1. As the capsule (1) is absent, the support layer (12) of FIG. 1 is not required in the embodiment described in FIG. 5.

Figures 6A, 6B, 6C:
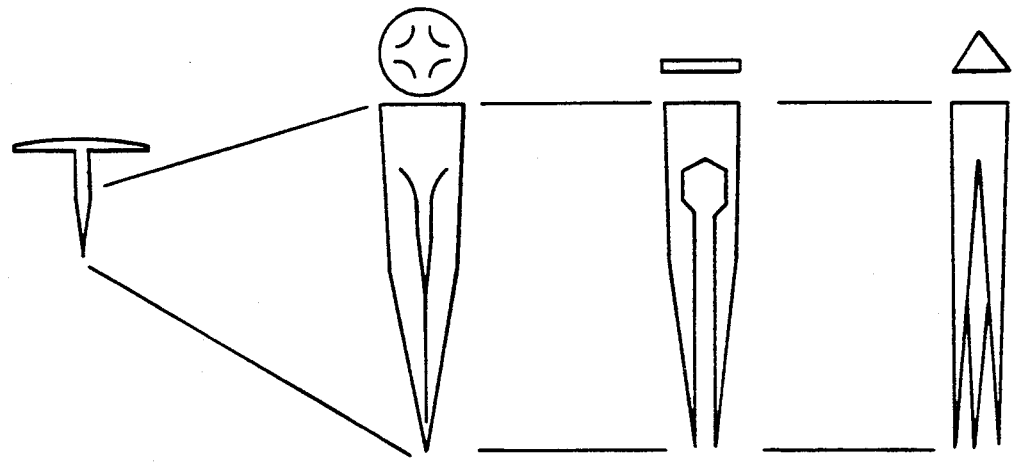

FIG. 6 shows alternative needle configurations which may be used in the skin test device, to enhance the delivery of antigen to the skin. (A) depicts a needle with a grooved shaft, (B) depicts a needle with twin points, (C) depicts a needle with multiple points.

Figure 7:
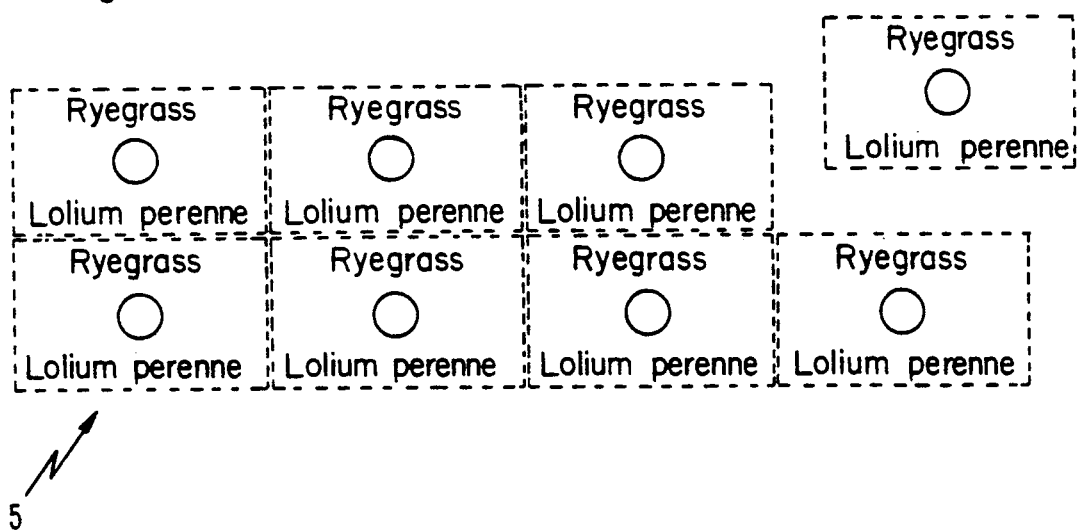
FIG. 7 shows the view from above of patch-like embodiments of the invention.

FIG. 7 depicts a preferred embodiment of the individual skin test units containing the same single antigen solution arranged in a sheet form, so that the single units can be individually separated.

The units of FIG. 7 are illustrated in more detail in FIG. 10. The antigen solution (1) is contained within a reservoir into which the needle (3) projects. The top covering layer (14) which could be made of a flexible material such as an ionomer resin, e.g., Surlyn (Registered Trade Mark) is domed at (14') to provide the space which the needle (3) and reservoir (5) occupy. A transparent layer (10) is provided adjacent the reservoir and has a hole (18) to permit the antigen solution to reach the skin when the device is in use. The device is sealed with a bottom layer (9).

FIG. 8 illustrates a preferred embodiment of the invention where multiple antigen tests can be performed at the same time. A side view of the embodiment of FIG. 8 is illustrated in FIG. 9.

FIG. 11 shows greater detail of the transparent layer shown in the previous figures, for the format of the skin test units shown in FIG. 8. The embodiment illustrated is marked with a callibrated scale, enabling a skin reaction response to be recorded on this layer along with details of the subject or patient and test date.

The volume of antigen associated with each unit is sufficient for a single test. The aqueous solution of the antigen may contain components other than the antigen itself. Such components may be added, for example, to increase the stability of the antigen, reduce the non-specific binding of the antigen to surfaces, maintain solubility, reduce evaporation, protect against contamination by microorganisms or as a buffer. Examples of such added substances include ionic salts, non-reactive carrier proteins such as human serum albumin, non-ionic detergents, glycerol and anti-bacterial and anti-fungal agents.

The needle is to be constructed of a material to ensure sharpness, allow sterilisation and be easily manufactured. Some examples of such materials may be hard plastic, steel and nylon. The needle may penetrate the skin with a single point or may possess several points and may also contain features, such as fluting or grooves to improve the flow of the antigen solution into the puncture site.

The application of this design may not be restricted to in vivo testing of the immune response to antigens. Another application of this device could be the delivery of biological or non-biological material into the skin for purposes other than for diagnosis. Such material could be of microbiological origin to function as a vaccine, immunoreactive material to stimulate an immune response, or a therapeutic drug or other substance. This type of application may require minor modification to the needle. For example, the needle in FIG. 4 would have the outlet lower down the shaft towards the point to force more antigen into the puncture site rather than as shown, where the needle is designed to flood the site allowing passive infiltration.

It may also be preferred to incorporate into the layer in contact with the skin, as well as the weak adhesive, an absorbent band between antigen reservoir sites, so that excess antigen solution is not forced from one test site to an adjacent site giving rise to false positive reactions.

It may also be preferred to incorporate into the layer in contact with the skin a mild, topical, local anaesthetic which would not interfere with the skin test response, but would reduce the itching and minor discomfort associated with an immediate skin test reaction.

Gamma irradiation may be used for sterilisation of the devices of the invention.

INDUSTRIAL APPLICABILITY

Medical devices of the invention enable allergy and other skin tests to be readily performed by medical and paramedical personnel to provide a quick result and permanent record.

We claim:

1. A medical testing device adapted to be held against the skin of a patient to perform a test, said device comprising:
    a hollow body having wall means defining a sealed chamber containing a test reagent therein,
    a releasably attachable transparent layer releasably connected to the body and including calibrated indicia to enable a test result to be measured, said transparent layer forming a skin engaging surface of the device and, in use, being located against the patient's skin,
    a needle connected to said hollow body and being located within the body, said needle having at least one point extending toward said transparent layer and being moveable to extend beyond said body to penetrate the patient's skin to a predetermined depth,
    said device being adapted to be depressible by a user to cause the needle to penetrate said wall means of said chamber and release said reagent therefrom, said point extending beyond said transparent layer into the patient's skin to said predetermined depth to cause said reagent to flow thereto.

2. The device according to claim 1, further comprising a bottom cover removably affixed to said transparent layer.

3. The device according to claim 1, wherein said needle has a plurality of points facing, in use, said transparent layer, to enhance flow of the reagent to the skin.

4. The device according to claim 1, wherein said needle is fluted to enhance flow of the reagent to the skin.

5. The device according to claim 1, wherein said needle is grooved to enhance flow of the reagent to the skin.

6. The device according to claim 1, wherein the cross section of the needle is enlarged to prevent penetration of the skin beyond the predetermined depth.

7. The device according to claim 1, wherein the test reagent is an antigen.

8. The device according to claim 1, wherein the test reagent further contains a stabilizer.

9. The device according to claim 1, wherein the test reagent further contains a preservative.

10. The device according to claim 1, wherein the test reagent further contains a buffer.

11. The device according to claim 1, wherein the test reagent is contained within a capsule or reservoir disposed within the hollow body.

12. The device according to claim 11, wherein the needle is provided with at least one further point facing in a direction opposite said point facing said transparent layer and the capsule is located adjacent the further point or points.

13. The device according to claim 1, wherein the test reagent is contained within a porous matrix.

14. The device according to claim 1, wherein the test reagent contains an additive to form a paste.

15. The device according to claim 1, wherein the test reagent contains an additive to form a gel.

16. The device according to claim 1, wherein the transparent layer has a surface capable of being written on so that the result of the test can be recorded thereon.

17. The device according to claim 1, wherein the body of the device is provided with a structure deformable to reduce the volume of said chamber.

18. The device according to claim 11, wherein a collapsible layer is provided within said body and surrounding said capsule or reservoir which permits the volume of the chamber to be reduced on application of pressure to the device.

19. A medical testing device comprising at least one of a strip or sheet containing a plurality of testing devices, each device comprising:
   a hollow body having wall means defining a sealed chamber containing a test reagent therein,
   a releasably attachable transparent layer releasably connected to the body and including calibrated indicia to enable a test result to be measured, said transparent layer forming a skin engaging surface of the device and, in use, being located against the patient's skin,
   a needle connected to said hollow body and being located within the body, said needle having at least one point extending toward said transparent layer and being moveable to extend beyond said body to penetrate the patient's skin to a predetermined depth,
   said device being adapted to be depressible by a user to cause the needle to penetrate said wall means of said chamber and release said reagent therefrom, said point extending beyond said transparent layer into the patient's skin to said predetermined depth to cause said reagent to flow thereto, each of said devices containing a different test reagent in its associated sealed chamber.

20. A medical testing device adapted to be held against the skin of a patient to perform a test, said device comprising:
   a hollow body containing a test reagent therein,
   a releasably attachable transparent layer releasably connected to the body and including calibrated indicia to enable the test result to be measured, said transparent layer forming a skin engaging surface of the device and which, in use, is located against the skin of the patient,
   a needle located within the hollow body and coated by said test reagent, said needle having at least one point facing said transparent layer and being moveable to extend beyond said body to penetrate the patient's skin to a predetermined depth,
   and wherein said device is adapted to be depressible by a user to cause said point to extend beyond said transparent layer and penetrate into the patient's skin to a predetermined depth and to cause said reagent to flow thereto.

21. A method of testing for an immune response with a medical testing device including a hollow body having wall means defining a sealed chamber containing a test reagent therein, a releasably attachable transparent layer connected to the body and including calibrated indicia to enable a test result to be measured, a needle connected to the body and being located within the device, said needle having a least one point facing the transparent layer of the device, comprising the steps of:
   (a) attaching the device to the patient's skin by affixing the releasably attachable transparent layer against the skin;
   (b) manipulating said needle so that it penetrates the sealed chamber and extends beyond the body and transparent layer to penetrate the patient's skin, said needle by penetrating the wall means of the chamber causing reagent to be released therefrom through the transparent layer and into the patient's skin; and
   (c) removing the hollow body by separating it from the releasably attachable transparent layer, said transparent layer remaining against the patient's skin.

* * * * *